(12) United States Patent
Nakahara et al.

(10) Patent No.: US 9,022,569 B2
(45) Date of Patent: May 5, 2015

(54) OPHTHALMOLOGIC APPARATUS, CONTROL METHOD THEREFORE, AND RECORDING PROGRAM EXECUTING THE METHOD

(75) Inventors: Yasuhiro Nakahara, Kawasaki (JP); Shigeaki Ono, Tokyo (JP); Hiroki Uchida, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 116 days.

(21) Appl. No.: 13/598,729

(22) Filed: Aug. 30, 2012

(65) Prior Publication Data
US 2013/0194094 A1 Aug. 1, 2013

(30) Foreign Application Priority Data
Jan. 26, 2012 (JP) .................................. 2012-014648

(51) Int. Cl.
*A61B 3/14* (2006.01)
*A61B 3/10* (2006.01)
*A61B 3/00* (2006.01)

(52) U.S. Cl.
CPC .......................................... *A61B 3/14* (2013.01)

(58) Field of Classification Search
USPC .................................................. 351/208, 245
See application file for complete search history.

(56) References Cited

U.S. PATENT DOCUMENTS

| 5,508,760 | A |   | 4/1996  | Kobayashi et al. |
| 5,894,337 | A |   | 4/1999  | Okinishi et al. |
| 5,940,165 | A | * | 8/1999  | Isogai et al. .................. 351/208 |
| 6,192,269 | B1 |  | 2/2001  | Okumura et al. |
| 6,332,683 | B1 |  | 12/2001 | Ono et al. |
| 6,337,993 | B1 |  | 1/2002  | Kishida et al. |
| 6,535,757 | B2 |  | 3/2003  | Ono |
| 6,569,104 | B2 |  | 5/2003  | Ono et al. |
| 6,834,202 | B2 |  | 12/2004 | Ono |
| 7,488,071 | B2 |  | 2/2009  | Ogawa et al. |
| 7,830,525 | B2 |  | 11/2010 | Buckland et al. |

(Continued)

FOREIGN PATENT DOCUMENTS

| CN | 101507601 A | 8/2009 |
| JP | 3386839 B2  | 3/2003 |

(Continued)

OTHER PUBLICATIONS

Jul. 1, 2014 Chinese Official Action in Chinese Patent Appln. No. 201310030688.3.

*Primary Examiner* — Jordan Schwartz
(74) *Attorney, Agent, or Firm* — Fitzpatrick, Cella, Harper & Scinto

(57) ABSTRACT

When an anterior segment photographing mode is selected, ease of operation by an inspector is improved. An ophthalmologic apparatus includes an area changing unit for changing a movement area of an optical unit including an optical path of measuring light, when an anterior segment photographing mode for photographing an anterior segment of an eye to be inspected is selected, to be different from a movement area when a mode other than the anterior segment photographing mode is selected.

12 Claims, 8 Drawing Sheets

(56) References Cited

U.S. PATENT DOCUMENTS

| | | |
|---|---|---|
| 7,841,717 B2 | 11/2010 | Ito et al. |
| 7,980,696 B1 | 7/2011 | Taki et al. |
| 2009/0128778 A1* | 5/2009 | Honda et al. .................. 351/245 |
| 2009/0207378 A1 | 8/2009 | Ito et al. |
| 2011/0176111 A1* | 7/2011 | Taki et al. .................... 351/207 |
| 2012/0002164 A1* | 1/2012 | Yamamoto et al. ........... 351/206 |
| 2012/0044499 A1 | 2/2012 | Shimoyama et al. |
| 2012/0050670 A1 | 3/2012 | Nakahara et al. |
| 2012/0075640 A1 | 3/2012 | Sakagawa et al. |
| 2012/0249953 A1 | 10/2012 | Ono |
| 2012/0249954 A1 | 10/2012 | Uchida |

FOREIGN PATENT DOCUMENTS

| | | |
|---|---|---|
| JP | 2007-282672 A | 11/2007 |
| JP | 2009-189624 A | 8/2009 |
| JP | 2010-246740 A | 11/2010 |
| JP | 2011-005005 A | 1/2011 |
| JP | 2011-147609 A | 8/2011 |
| JP | 2011-147612 A | 8/2011 |

* cited by examiner

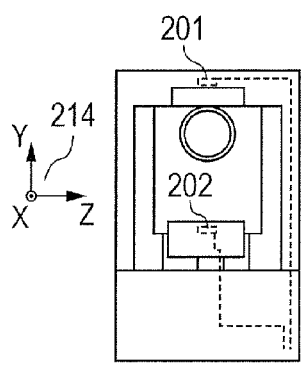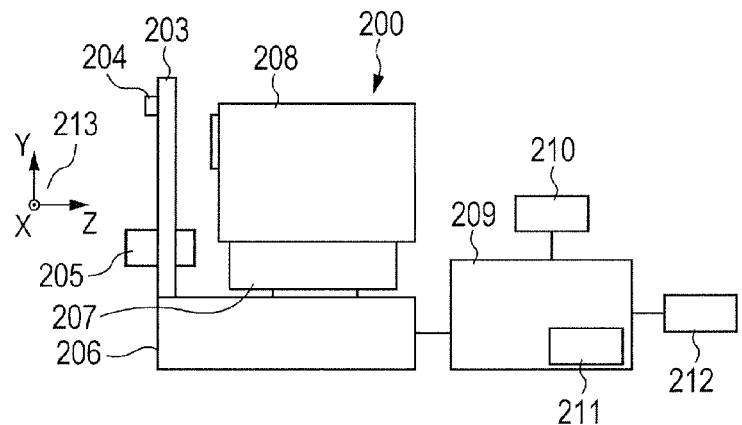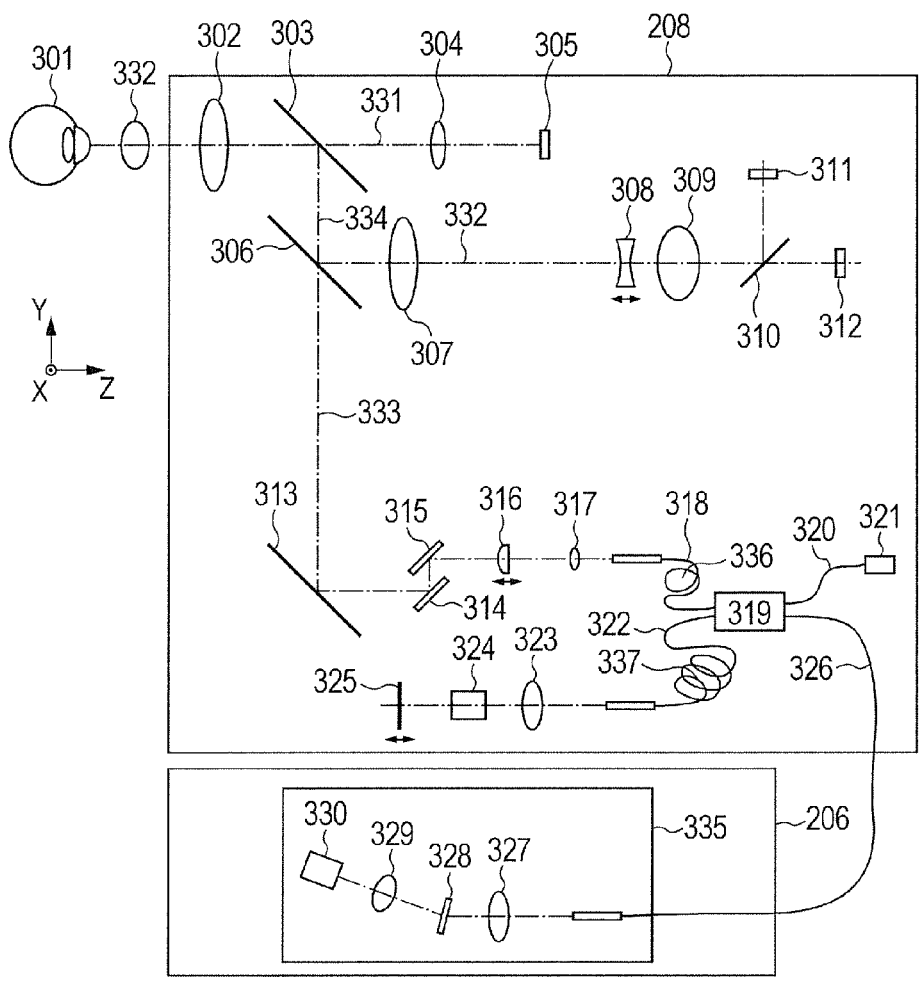

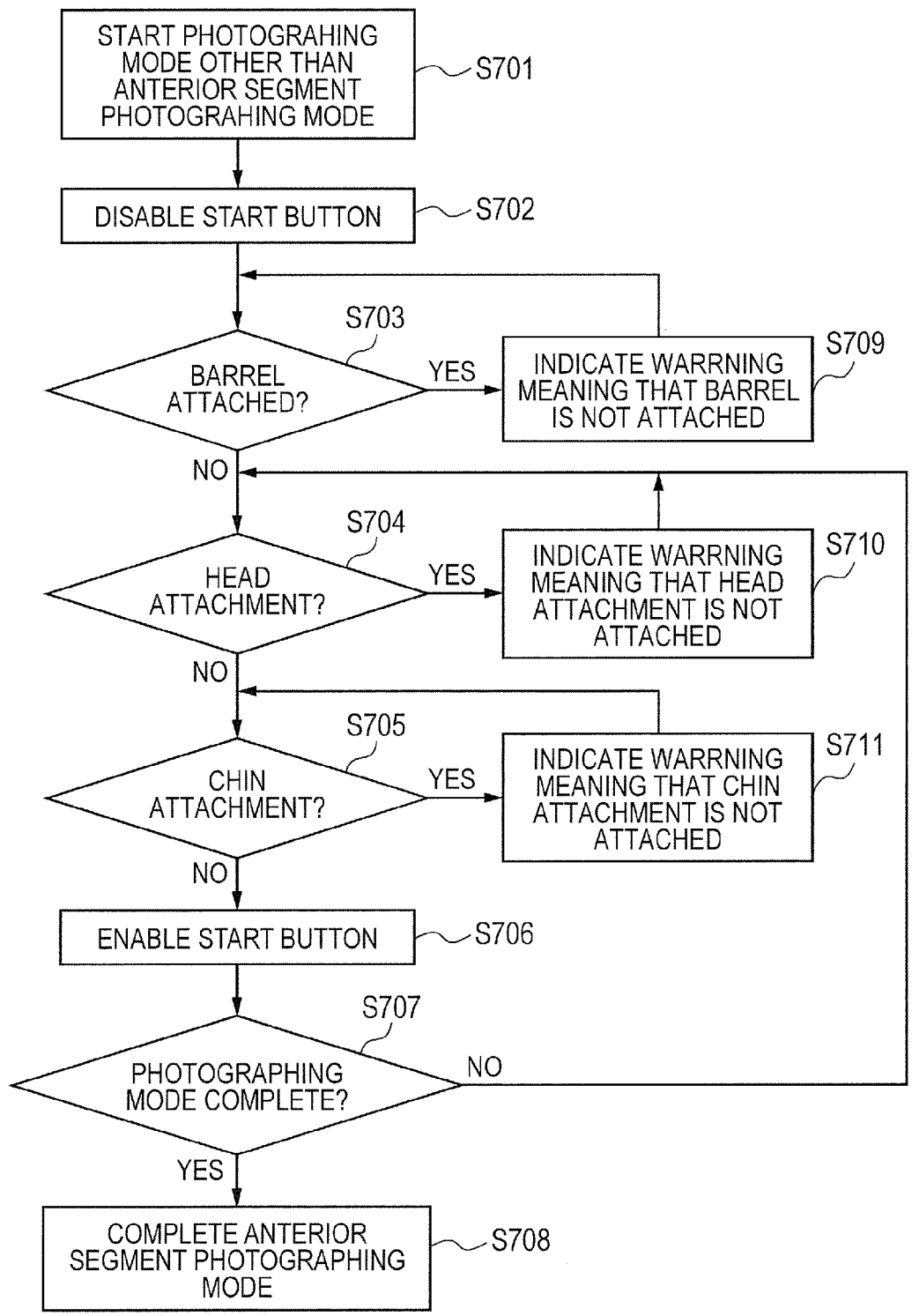

OPHTHALMOLOGIC APPARATUS, CONTROL METHOD THEREFORE, AND RECORDING PROGRAM EXECUTING THE METHOD

BACKGROUND OF THE INVENTION

1. Field of the Invention

The present invention relates to an ophthalmologic apparatus for acquiring an image of an eye to be inspected, a method of controlling the ophthalmologic apparatus, and a program for causing a computer to perform the control method.

2. Related Background Art

Ophthalmologic apparatus such as optical coherence tomography (OCT) and a fundus camera can acquire images of a fundus and an anterior segment. These ophthalmologic inspection apparatus are required to focus on the fundus segment and the anterior segment. Therefore, the focusing on the fundus segment and on the anterior segment is obtained by disposing an optical head having a so-called large Z axis stroke, by attaching detachable forehead rest and chin rest members, or by disposing a detachable optical element outside the apparatus (see Japanese Patent No. 3,386,839 and U.S. Pat. No. 7,830,525).

When the above-mentioned Z axis stroke is enlarged, the main body becomes large. Therefore, usually, the forehead rest and the chin rest are used together with that in many cases. However, in this case, it may be forgotten to attach the attachment member in an anterior segment photographing mode, or to detach the attachment member in a mode other than the anterior segment photographing mode. In addition, when the attachment member is attached in front of an objective lens, a distance between the apparatus main body and the eye to be inspected is decreased compared with fundus photography. Therefore, the operation must be performed carefully.

SUMMARY OF THE INVENTION

It is one of the objects of the present invention to improve ease of operation by an inspector when the anterior segment photographing mode is selected.

In order to achieve solution of the above-mentioned problems, according to the present invention, there is provided an ophthalmologic apparatus configured to acquire an image of an eye to be inspected based on return light from the eye to be inspected irradiated with measuring light, the ophthalmologic apparatus including: a photographing mode selecting unit configured to select any one of a plurality of photographing modes including an anterior segment photographing mode for photographing an anterior segment of the eye to be inspected; a moving unit configured to move an optical unit including an optical path of the measuring light with respect to the eye to be inspected; and an area changing unit configured to change a movement area of the optical unit, in a case where the anterior segment photographing mode is selected, to be different from a movement area in a case where a mode other than the anterior segment photographing mode is selected.

Further features of the present invention will become apparent from the following description of exemplary embodiments with reference to the attached drawings.

BRIEF DESCRIPTION OF THE DRAWINGS

FIGS. 2A and 2B are diagrams schematically illustrating a configuration of an ophthalmologic apparatus according to a first embodiment of the present invention.

FIG. 3 is a diagram schematically illustrating a configuration of a measurement optical system and a spectroscope of the ophthalmologic apparatus according to the first embodiment of the present invention.

FIG. 7 is a diagram illustrating a flowchart when the inspection set is set to a mode other than the anterior segment photographing mode in the first embodiment of the present invention.

DESCRIPTION OF THE EMBODIMENTS

Figure 1:
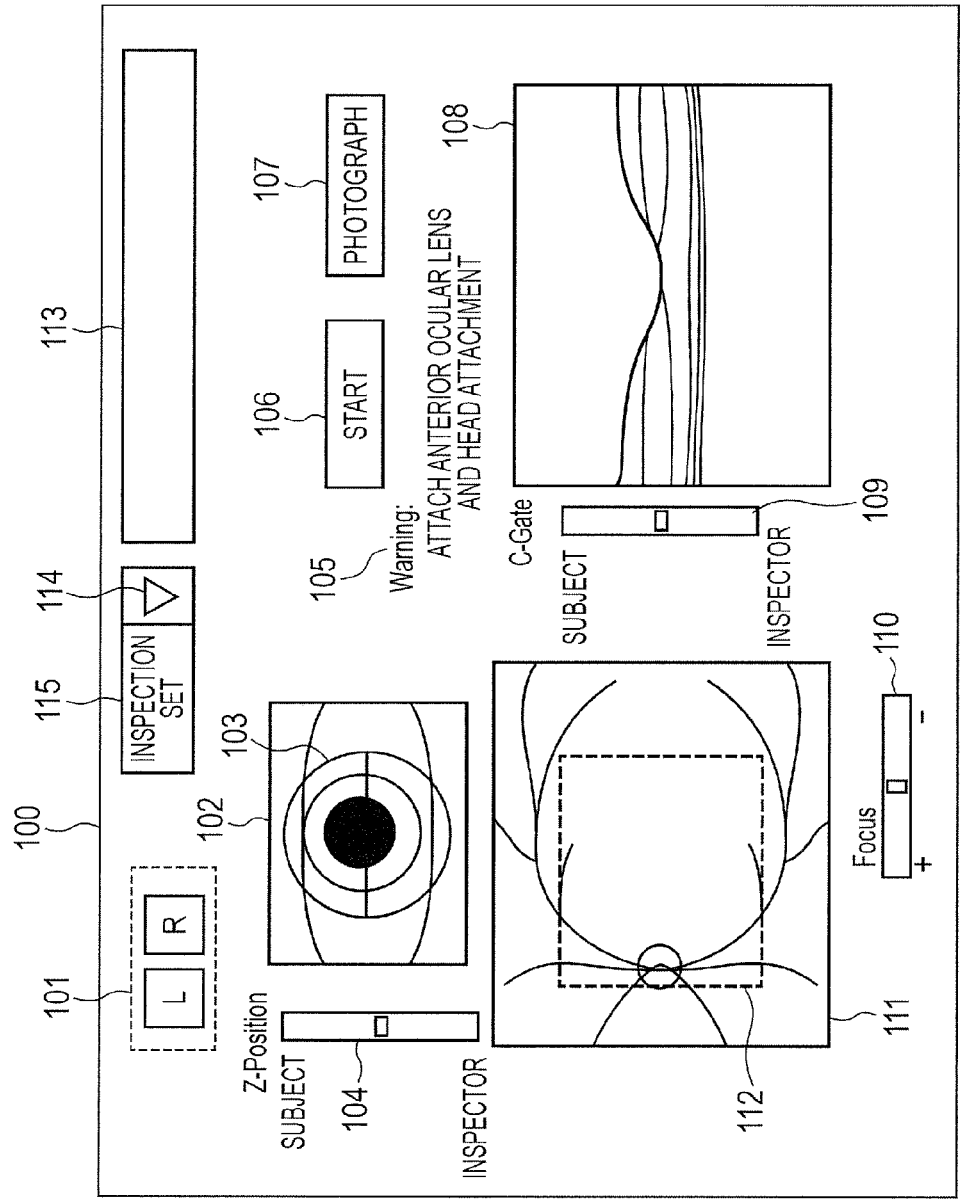
FIG. 1 is a diagram illustrating one aspect of a capture screen displaying images of an eye to be inspected and others according to an embodiment of the present invention.

Preferred embodiments of the present invention will now be described in detail in accordance with the accompanying drawings.

First Embodiment

With reference to the drawings, an ophthalmologic apparatus according to a first embodiment of the present invention and an operation flow thereof are described.

(Configuration of Main Body)

FIG. 2B is a side view of the ophthalmologic apparatus according to the first embodiment. Reference numeral 200 denotes an ophthalmologic apparatus; 208, an optical head that is a measurement optical system for acquiring an image of an anterior segment, and a two-dimensional image and a tomographic image of a fundus; and 207, a stage portion that is a moving portion capable of moving the optical head through use of motors (not shown) in xyz directions. Reference numeral 206 denotes a base portion containing a spectrometer (described later).

Reference numeral 209 denotes a personal computer which also serves as a control portion of the stage portion, controls the stage portion, and configures a tomographic image to be described later. Reference numeral 211 denotes a hard disk which also serves as a subject information storage portion, an inspection set storage unit, and a scanning control unit, and stores a program and the like for photographing a tomographic image. Reference numeral 210 denotes a monitor which serves as a display portion; and 212, an input portion by which an instruction to the personal computer is input, and specifically, includes a keyboard and a mouse. Reference numeral 203 denotes a face rest which holds a chin and a forehead of a subject to urge the subject to fix an eye. Reference numeral 204 denotes a silicone rubber member for receiving the forehead of a subject (hereinafter referred to as a forehead rest). Reference numeral 205 denotes a member for receiving the chin of the subject, which is moved by an actuator (not shown) in a Y axis direction by a stroke of 30 mm so that the height of the eye to be inspected is adjusted (hereinafter referred to as a chin rest). FIG. 2A is a front view of the ophthalmologic apparatus according to the first embodiment. A Hall device 201 is mounted inside the case on the upper side of the mounting portion of the above-mentioned silicone rubber member 204 for receiving the forehead. A Hall device 202 is also mounted inside the member 205 for receiving the chin. The Hall devices 201 and 202 are connected to a CPU board (not shown) disposed inside the ophthalmologic inspection apparatus 200 so as to detect a magnetic field.

Note that, the chin rest for receiving the chin of the subject and the forehead rest for receiving the forehead are one aspect of the attachment member of this embodiment, and it is sufficient that at least one thereof be used. In addition, the attachment members are attached to the ophthalmologic apparatus and act so that a focal position of the ophthalmologic apparatus is moved to the anterior segment.

(Configurations of Measurement Optical System and Spectroscope)

Configurations of the measurement optical system and the spectroscope of this embodiment are described with reference to FIG. 3. First, an inside of the optical head 208 is described. An objective lens 302 is disposed to be opposed to an eye to be inspected 301. Reference numeral 332 denotes an anterior segment observation lens which can be attached/detached to/from an objective lens barrel (not shown) by a filter thread formed inside, and is attached when the anterior segment is photographed. An optical axis of the objective lens is split by a first dichroic mirror 303 into an anterior segment observing optical path 331 and an optical path 334 for OCT, fundus observation, and an internal fixation lamp. Then, the optical path 334 is split by a second dichroic mirror 306 into an optical path 333 of an OCT optical system and an optical path 332 for fundus observation and an internal fixation lamp.

The optical path 332 is further split by a third dichroic mirror 310 into an optical path to a CCD 311 for fundus observation and an optical path to a fixation lamp 312 in accordance with their wavelength bands in the same manner as described above. Here, reference numerals 308 and 309 denote lenses, and the lens 308 is driven by a motor (not shown) for focusing of the fixation lamp and fundus observation. The CCD 311 has a sensitivity at a wavelength of illumination light (not shown) for fundus observation, specifically at a wavelength of approximately 780 nm. On the other hand, the fixation lamp 312 generates visible light so as to prompt the subject to stare.

In the optical path 331, reference numeral 304 denotes a lens and reference numeral 305 denotes an infrared CCD for anterior segment observation. The CCD 305 has sensitivity at a wavelength (not shown) for anterior segment observation, specifically at a wavelength of approximately 970 nm.

The optical path 333 constitutes the OCT optical system as described above, and is used for photographing the tomographic image of the fundus of the eye to be inspected 301. More specifically, the optical path 333 is used for acquiring an interference signal for forming the tomographic image. Reference numerals 314 and 315 denote XY scanners for scanning the fundus with light. Reference numerals 316 and 317 denote lenses, and the lens 316 is driven by a motor (not shown) so as to focus light from an OCT light source 321 emerging from a fiber 318 connected to an optical coupler 319 on the fundus of the eye to be inspected 301. By this focusing operation, light from the fundus of the eye to be inspected 301 form images as a spot on an end of the fiber 318 simultaneously and enters the end thereof.

Next, configurations of an optical path from the OCT light source 321, a reference optical system, and a spectroscope 335 are described.

Reference numeral 321 denotes the OCT light source; 325, a mirror; 324, a dispersion compensating glass; 319, the above-mentioned optical coupler; 318, 320, 322, and 326, single-mode optical fibers connected and integrated to the optical coupler; 323, a lens; and 335, the spectroscope.

These elements constitute a Michelson interferometer. The light emitted from the OCT light source 321 passes through the optical fiber 320 and is split by the optical coupler 319 into the measuring light on the optical fiber 318 side and the reference light on the optical fiber 322 side. The measuring light irradiates the fundus of the eye to be inspected 301 as an observation target via the optical path of the above-mentioned OCT optical system and is reflected or scattered by the retina to reach the optical coupler 319 via the same optical path.

The optical coupler 319 combines the measuring light with the reference light to be interference light. Here, the interference occurs when an optical path length of the measuring light becomes almost the same as an optical path length of the reference light. The mirror 325 is retained in an adjustable manner in an optical axis direction by a motor (not shown) and a drive mechanism (not shown), and hence the optical path length of the reference light can be adjusted to the optical path length of the measuring light that varies depending on the eye to be inspected 301. The interference light is guided to the spectroscope 335 via the optical fiber 326.

In addition, reference numeral 336 denotes a polarization adjustment portion on the measuring light side disposed in the optical fiber 318. Reference numeral 337 denotes a polarization adjustment portion on the reference light side disposed in the optical fiber 322. The polarization adjustment portions include some parts in which the optical fiber is looped, and the looped part is turned about a center line of the fiber in a longitudinal direction of the fiber so that the fiber is twisted. Thus, polarized states of the measuring light and the reference light can be adjusted respectively to the same state. The spectroscope 335 is formed of lenses 327 and 329, a diffraction grating 328, and a line sensor 330. The interference light emerged from the optical fiber 326 becomes collimated light via the lens 327, and is then diffracted by the diffraction grating 328 so as to form images on the line sensor 330 via the lens 329.

Next, a periphery of the OCT light source 321 is described. The OCT light source 321 is a super luminescent diode (SLD) that is a typical low coherent light source. The center wavelength is 855 nm, and the wavelength band width is approximately 100 nm. Here, the bandwidth is an important parameter because it affects a resolution of the acquired tomographic image in the optical axis direction. In addition, the SLD is selected as a type of the light source here, but it is sufficient as long as the light source can emit low coherent light. It is possible to use an amplified spontaneous emission (ASE) or the like. As to the center wavelength, near-infrared light is suitable in view of measuring an eye. In addition, because the center wavelength affects the resolution of the acquired tomographic image in a lateral direction, it is desired that the wavelength be as short as possible. Therefore, the center wavelength is set to 855 nm because of both reasons.

The Michelson interferometer is used in this embodiment, but a Mach-Zehnder interferometer may be used. In accordance with a light intensity difference between the measuring light and the reference light, it is desired to use the Mach-Zehnder interferometer when the light intensity difference is large, and to use the Michelson interferometer when the light intensity difference is relatively small.

Note that, in the optical system and the like described above, members for obtaining image information of the fundus segment of the subject, and the personal computer 209 and a CPU described later for operating the members are referred to generically as a fundus information acquiring unit. In addition, in the same manner, members for obtaining image information of the anterior segment of the subject, and the personal computer 209 and the CPU described later for operating the members are referred to generically as an anterior segment information acquiring unit. In addition, the above-mentioned configuration of the optical system and the like functions as an optical head for irradiating light to the anterior segment and receiving reflected light from the anterior segment in the ophthalmologic apparatus.

(Method of Photographing Tomographic Image)

A method of photographing the tomographic image using the ophthalmologic inspection apparatus 200 is described. The ophthalmologic apparatus 200 can photograph the tomographic image of a predetermined part of the eye to be inspected 301 by controlling the XY scanners 314 and 315.

First, measuring light 321 scans in an X direction in FIG. 3 so that the line sensor 330 photographs information of a predetermined number of lines in a photographing range of the fundus in the x direction. The fast Fourier transform (FFT) is performed on a luminance distribution on the line sensor 330 obtained at a certain position in the X direction, and information obtained by the FFT from the linear luminance distribution is converted into density or color information to be displayed on the monitor 210. This converted information is referred to as an A-scan image. A two-dimensional image on which a plurality of A-scan images is arranged is referred to as a B-scan image. After a plurality of A-scan images is photographed for organizing one B-scan image, the scan value in a Y direction is moved, and the scanning in the X direction is performed again so that a plurality of B-scan images is acquired.

The plurality of B-scan images or a three-dimensional image organized from the multiple B-scan images is displayed on the monitor 210 so as to be used for diagnosis of the eye to be inspected by the inspector. The example in which the B-scan image is acquired by scanning in the X direction is described above, but this is not a limitation. It is possible to acquire the B-scan image by scanning in the Y direction. In addition, it is possible to acquire the B-scan image by an arbitrary scanning pattern with scans in both the X direction and the Y direction.

(Inspection Set)

An inspection set is described. There are many types of loci in the scanning pattern. For instance, there are a line scan, a cross line scan, a multi-line scan, a circle scan, a radial scan, and the like. In order to perform an appropriate inspection for various lesions, it is necessary to determine an appropriate scanning pattern among them. In addition, depending on the lesion, it is necessary to inspect using a plurality of scanning patterns.

A scanning pattern storage portion stores in advance scanning patterns suitable for the lesions to be inspected. For instance, for a disease of the macula lutea portion, a 3D scan for scanning the entirety and a cross scan in the horizontal and vertical directions are stored. For a disease of the optic disk, the horizontal line scan, the circle scan, and the like are stored.

In this way, by preparing in advance the scanning patterns suitable for the lesions, an appropriate inspection can be performed for each of various lesions. The inspector can only select an appropriate inspection set among the prepared inspection sets, and hence time and effort of the inspector can be reduced, and the throughput can be improved.

(Capture Screen)

FIG. 1 illustrates a capture screen. Reference numeral 102 denotes an anterior segment observation screen obtained by a CCD for anterior ocular observation; 111, a display screen of a two-dimensional fundus image, which is obtained by the CCD for anterior ocular observation; and 108, a tomographic image display screen for checking an acquired tomographic image. Reference numeral 101 denotes buttons for switching a left eye and a right eye for an eye to be inspected, and the optical head 208 is moved to an initial position of a left or right eye by pressing an L or R button.

Reference numeral 115 denotes an inspection set selection screen, which displays a selected inspection set. In a case where the inspection set is changed, the inspector clicks 114 so that a pull-down menu (not shown) is displayed, and selects a desired inspection set. The pull-down menu (not shown) includes an anterior segment photographing mode. An action in a case where the anterior segment photographing mode is selected is described later. In addition, a scanning pattern display screen 113 displays the name of the scanning pattern to be performed in the currently selected inspection set, for example, the horizontal scan, the vertical scan, the cross scan, or the like.

In a case where an arbitrary point of the anterior segment observation screen 102 is clicked with a mouse, the optical head 208 is moved by an XYZ table (not shown) for performing alignment between the optical head and the eye to be inspected so that the point comes to the center of the screen. Reference numeral 106 denotes a start button. When this button is pressed, acquisition of a two-dimensional image and a tomographic image is started, and the acquired images of the eye to be inspected are displayed in real time in the two-dimensional image display screen 111 and the tomographic image display screen 108.

A slider disposed in the vicinity of each image is for adjustment. A slider 104 is for adjusting a Z direction position of the optical head with respect to the eye to be inspected, a slider 110 is for adjusting a focus, and a slider 109 is for adjusting a position of a coherence gate. The focus adjustment is an adjustment by moving the lenses 308 and 316 in the illustrated directions so that the focus is adjusted on the fundus. The coherence gate adjustment is an adjustment by moving the mirror 325 in the illustrated direction so that the tomographic image can be observed in a desired position on the tomographic image display screen. These adjustment operations create a state in which the inspector can perform optimal photography. Reference numeral 107 denotes a photography button. After various adjustments are completed, this button is pressed so that a desired photography is performed.

Figure 5:
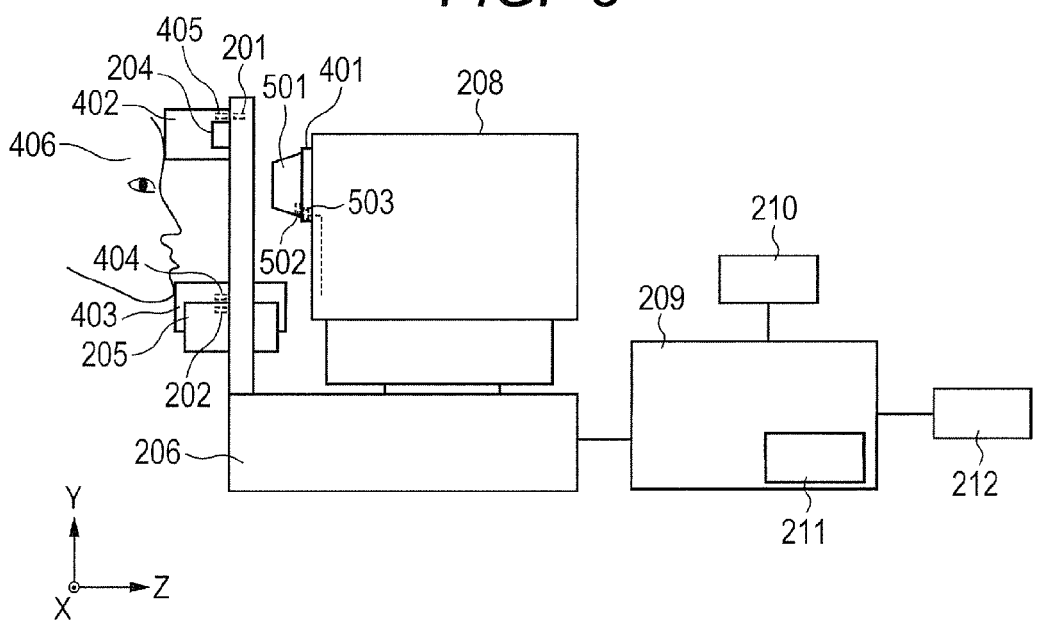
FIG. 5 is a side view illustrating a schematic configuration of the main body of the ophthalmologic apparatus in a state where an attachment member for anterior segment photography is attached in the first embodiment of the present invention.

FIG. 5 is a side view of the ophthalmologic apparatus to which the attachment member for the anterior segment photography is attached. Reference numeral 401 denotes an objective lens barrel unit. Reference numeral 402 denotes a member for adjusting a focal position to the anterior segment of a subject 406. The member 402 (hereinafter referred to as a forehead rest attachment) is made of silicone rubber. Reference numeral 405 denotes a magnet. The magnet 405 is incorporated inside the forehead rest attachment 402 and is attached to the face rest 203 so as to cover the forehead rest 204. Further, a hook and loop fastener or an attach/detach mechanism (not shown) is disposed so as to prevent a drop from the face rest 203. In a case where attaching to the face rest 203 so as to cover the forehead rest 204, the Hall device 201 responds to the magnetic field, and the CPU (not shown) disposed inside the ophthalmologic apparatus 200 detects that the forehead rest attachment 402 is attached to the main body. Reference numeral 403 denotes a member for adjusting the focal position to the anterior segment of the subject 406. The member 403 (hereinafter referred to as a chin rest attachment) is made of silicone rubber. Reference numeral 404 denotes a magnet. The magnet 406 is incorporated inside the chin rest attachment 403 and is attached to the chin rest 205 so as to cover the chin rest 403. In a case there the chin rest attachment 403 is set to cover the chin rest 205, the Hall device 202 responds to the magnetic field, and the CPU (not shown) disposed inside the ophthalmologic apparatus 200 detects that the chin rest attachment is attached to the chin rest portion. Reference numeral 501 denotes a barrel in which the anterior segment photographing lens 332 is incorporated. Therefore, in this case, the attachment members include an optical element to be attached in front of the objective lens. The barrel 501 is screwed into a filter thread portion (not shown) of the objective lens barrel unit 401 and is attached to the ophthalmologic inspection apparatus 200. Reference numeral 502 denotes a magnet. The magnet 502 is incorporated in the vicinity of the filter thread of the barrel 501. Reference numeral 503 denotes a Hall device. The Hall device 503 is electrically connected to the CPU (not shown) disposed inside the ophthalmologic apparatus 200. When the barrel 501 is screwed into the filter thread portion (not shown) of the objective lens barrel unit 401 and is attached to the ophthalmologic inspection apparatus 200, the Hall device 503 responds to the magnet 502, and the CPU (not shown) disposed inside the ophthalmologic inspection apparatus 200 detects that the barrel 501 is attached to the ophthalmologic apparatus 200. The example in which the Hall device is used for detecting the above-mentioned anterior segment photographing attachment members 402, 403, and 501 is described above, but it is possible to detect the attachment using a capacitance type distance sensor or a switch type sensor.

Note that, a sensor such as the Hall device for determining whether or not the attachment member to be attached to the ophthalmologic apparatus is attached, and a determination module region of the CPU or the personal computer 209 which actually determines whether or not the attachment member is attached based on a signal obtained from the sensor are referred to generically as a determining unit. The determining unit also determines whether or not the anterior segment photographing mode is selected by a photographing mode selecting unit described later. In addition, as the attachment member, the optical element or the like attached on the side closer to the eye to be inspected of the objective lens in the optical path of the measuring light is also exemplified as one aspect thereof.

Figure 6:
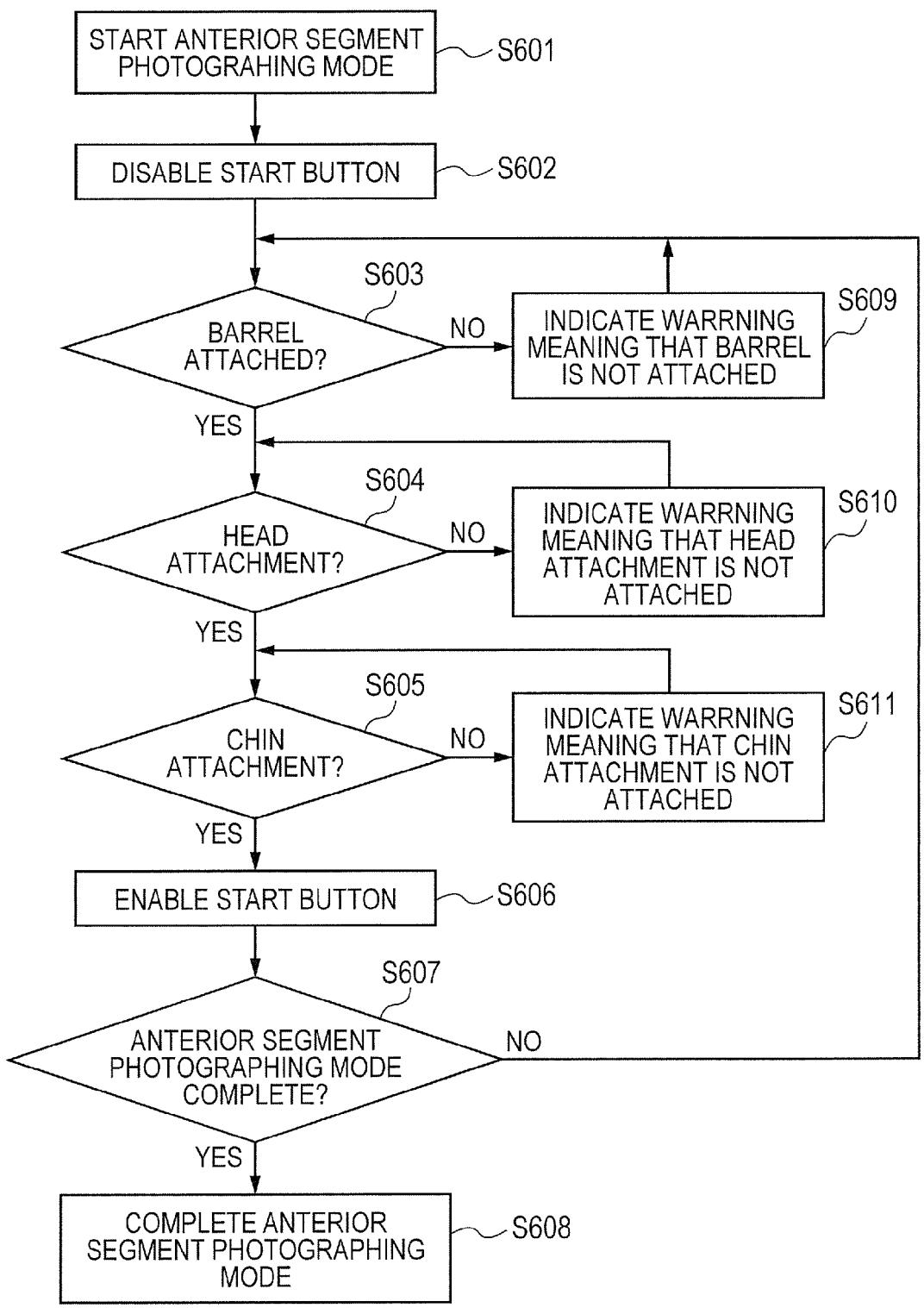
FIG. 6 is a diagram illustrating a flowchart when an inspection set is set to an anterior segment photographing mode in the first embodiment of the present invention.

FIG. 6 illustrates a flow in which the inspection set 115 is set to the anterior segment photographing mode. In S601, the photographing mode selecting unit sets the inspection set 115 to the anterior segment photographing mode. Selection of the anterior segment photographing mode is performed by a module region functioning as the photographing mode selecting unit for selecting the anterior segment photographing mode for acquiring image information of the anterior segment in the CPU or the personal computer 209. Next, the process proceeds to S602. In S602, the CPU disables the start button 106. In S603, the above-mentioned determining unit determines whether or not the barrel 501 is attached to the ophthalmologic apparatus 200. In a case where the barrel 501 is attached, the process proceeds to S604. In a case where the barrel 501 is not attached, the process proceeds to S609. In S609, a warning indicating that the barrel 501 is not attached is displayed in 105 of the display screen 100 constituting a display unit controlled by a display control unit, and then the process returns to S603. In S604, the determining unit determines whether or not the forehead rest attachment 402 is attached to the ophthalmologic apparatus 200. IN a case where the forehead rest attachment 402 is attached, the process proceeds to S605. IN a case where the forehead rest attachment 402 is not attached, the process proceeds to S610. In S610, a warning indicating that the forehead rest attachment 402 is not attached is displayed in 105 of the display screen 100 controlled by the display control unit, and the process returns to S604. In S605, the determining unit determines whether or not the chin rest attachment 403 is attached to the chin rest 205. In a case where the chin rest attachment 403 is attached, the process proceeds to S606. In a case where the chin rest attachment 403 is not attached, the process proceeds to S611. In S611, the display unit displays in 105 of the display screen 100 a warning indicating that the chin rest attachment 403 is not attached, and the process returns to S605. In S606, the CPU enables the start button 106. When reaching this step, all the attachment members related to the anterior segment observation and photography are attached, and hence the anterior segment photography can be certainly performed. In S607, it is determined whether or not the anterior segment photographing mode is completed. In a case where the anterior segment photographing mode is not completed, the process returns to S603. In a case where the anterior segment photographing mode is completed, the process proceeds to S608. In S608, the anterior segment photographing mode is completed.

The above-mentioned warning display functions as a warning unit for performing warning necessary to be notified to the inspector based on a result of the determination by the determining unit. In this case, it is preferred to specify a display form of at least one of the display indicating whether or not the anterior segment photographing mode is selected and the display indicating whether or not the attachment member is attached, and to dispose a module region in the control unit which functions as the display control unit instructing the display form to the display unit capable of functioning as one of the warning units. Further, in this case, if the determining unit determines that the attachment member is not attached to the ophthalmologic apparatus In a case where the anterior segment photographing mode is selected, or if the determining unit determines that the attachment member is attached to the ophthalmologic inspection apparatus In a case where the anterior segment photographing mode is not selected, the notification of warning to the inspector is performed in the warning unit, for example, in 105 of the display screen 100. However, it is possible to always display the above-mentioned display form related to the notification by the above-mentioned specific warning unit in 105. In addition, the notification of the warning by the warning unit or setting of a moving restricted area described later correspond to a predetermined operation of the ophthalmologic apparatus performed based on a result of the determination by the determining unit, and the predetermined operation is performed by the module region functioning as the control unit in the CPU or the personal computer 209. Note that, the determining unit may determine at least one of the selection of the anterior segment photographing mode and the attachment of the detachable attachment member to a predetermined place of the ophthalmologic apparatus. In this case, the control unit may perform the predetermined operation based on the determination result. In this case, it is preferred that the predetermined operation be the notification by the warning unit. In addition, as one aspect of the present invention, In a case where one of the selection of the anterior segment photographing mode and the attachment of the attachment member to the predetermined place is performed while the other is not performed, the display unit may indicate that the other is not performed in a specific display form instructed by the display control unit. Further, in this case, it is preferred that the display unit display that the attachment member is not attached or that the anterior segment photographing mode is not selected in a specific display form instructed by the display control unit. In addition, as one aspect of the present invention, the ophthalmologic apparatus for acquiring the image of the eye to be inspected based on return light from the eye to be inspected of the subject irradiated with measuring light also includes a configuration including the photographing mode selecting unit which selects the anterior segment photographing mode for acquiring the image of the anterior segment of the eye to be inspected, and the control unit which inserts the anterior segment photographing lens on the side closer to the eye to be inspected of the objective lens in the optical path of the measuring light In a case where the anterior segment photographing mode is selected.

FIG. 7 illustrates a flow when the inspection set 115 is set to a mode other than the anterior segment photographing mode.

In S701, the photographing mode selecting unit sets the inspection set 115 to a mode other than the anterior segment photographing mode. Next, the process proceeds to S702. In S702, the CPU disables the start button 106. In S703, the determining unit determines whether or not the barrel 501 is attached to the ophthalmologic inspection apparatus 200. In a case where the barrel 501 is attached, the process proceeds to S709. In a case where the barrel 501 is not attached, the process proceeds to S704. In S709, a warning indicating that the barrel 501 is attached is displayed by the display control unit in 105 of the display screen 100 constituting the display unit, and then the process returns to S703. In S704, the determining unit determines whether or not the forehead rest attachment 402 is attached to the ophthalmologic apparatus 200. In a case where the forehead rest attachment 402 is attached, the process proceeds to S710. In a case where the forehead rest attachment 402 is not attached, the process proceeds to S705. In S710, the display unit displays a warning indicating that the forehead rest attachment 402 is attached in 105 of the display screen 100, and the process returns to S704. In S705, the determining unit determines whether or not the chin rest attachment 403 is attached to the chin rest 205. In a case where the chin rest attachment 403 is attached, the process proceeds to S711. In a case where the chin rest attachment 403 is not attached, the process proceeds to S705. In S711, the display unit displays, in 105 of the display screen 100, a warning indicating that the chin rest attachment 403 is attached. In S706, the CPU enables the start button 106. When reaching this step, all the attachment members for the anterior segment observation and photographing mode are not attached, and hence a mode other than the anterior segment photographing mode can be certainly performed. In S707, the determining unit determines whether or not the mode other than the anterior segment photographing mode is completed. In a case where the mode other than the anterior segment photographing mode is not completed, the process returns to S703. In a case where the mode other than the anterior segment photographing mode is completed, the process proceeds to S708. In S708, the mode other than the anterior segment photographing mode is completed.

As described above, in a case where the anterior segment photographing mode is selected, the start button 106 does not become enabled unless the attachment members 402, 403, and 501 for anterior segment photography are attached to the ophthalmologic apparatus 200. In addition, in a case where the attachment members 402, 403, and 501 for the anterior segment photography are attached to the ophthalmologic apparatus 200 in a mode other than the anterior segment photographing mode, the start button 106 does not become enabled. Therefore, the attachment members for the anterior segment photographing mode can be certainly detached.

Second Embodiment

Figure 4:
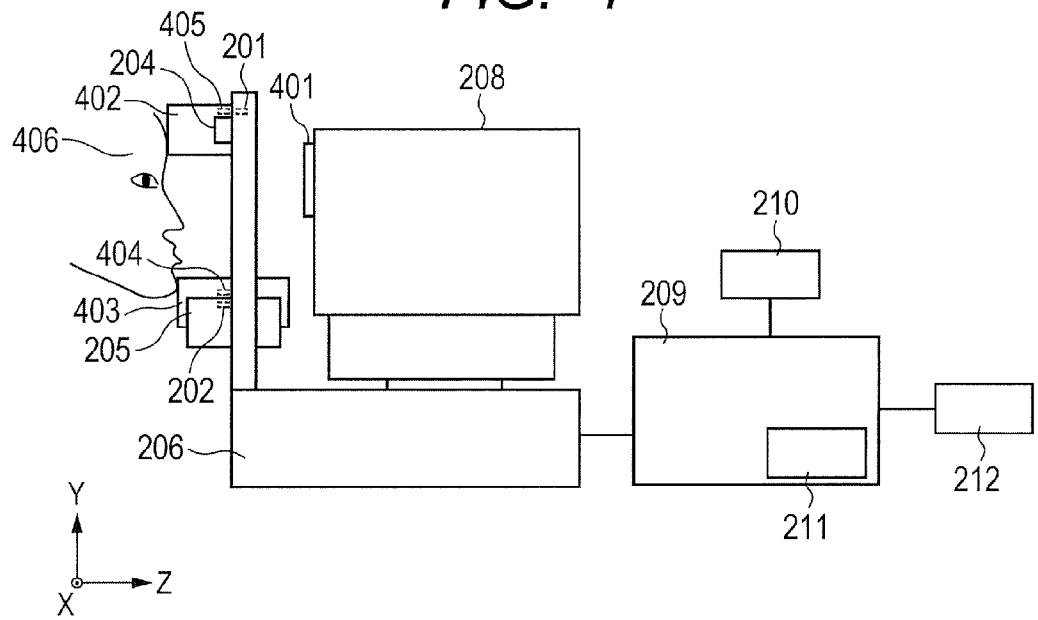
FIG. 4 is a side view illustrating a schematic configuration of a main body of an ophthalmologic apparatus according to a second embodiment of the present invention.

A second embodiment of the present invention is described with reference to the drawings. FIG. 4 is a side view of the ophthalmologic apparatus according to the second embodiment. The configurations of the measurement optical system and the spectroscope, the method of photographing the tomographic image, the inspection set, and the capture screen are the same as those in the first embodiment. As to a configuration of the main body, a moving amount in a direction of the Z axis of the optical head 208 is increased by 20 mm. Therefore, without attaching the barrel 501 described in the first embodiment, the anterior segment photography can be performed by attaching the forehead rest attachment 402 and the chin rest attachment 403. The specification of the configuration capable of the anterior segment photography is different from that in the first embodiment. In the operation flow, it is different that the determination parts in S603 of FIG. 6 and S703 of FIG. 7 and the branches S609 and S709 thereof are eliminated. As described above, in a case where the anterior segment photographing mode is selected, the start button 106 does not become enabled unless the attachment members 402 and 403 for the anterior segment photography are attached to the ophthalmologic apparatus 200. In addition, in a mode other than the anterior segment photographing mode, in a case where the attachment members 402 and 403 for the anterior segment photography are attached to the ophthalmologic apparatus 200, the start button 106 does not become enabled. Therefore, the attachment members for the anterior segment photographing mode can be certainly detached. In addition, the barrel 501 is not necessary in the configuration of this example. It may be added, however, that even in a case where only one attachment member is necessary in the anterior segment photographing mode, it is possible to embody in the same manner.

Third Embodiment

Figure 8A:
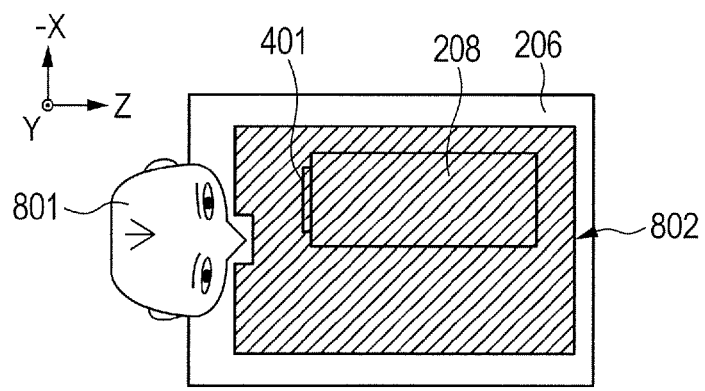
FIGS. 8A and 8B are top views illustrating a schematic configuration of a main body of an ophthalmologic apparatus according to a third embodiment of the present invention.
Figure 8B:
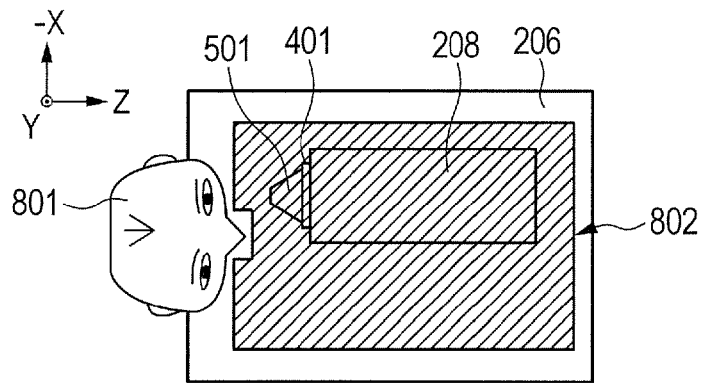

A third embodiment of the present invention is described with reference to the drawings. FIGS. 8A and 8B are top views of a main body of an ophthalmologic apparatus according to the third embodiment. In these drawings, for convenience sake of description, the face rest 203 is omitted. The configuration is different in that a new operation flow is added to the flowchart illustrated in the first embodiment. This flow is described later.

Reference numeral 801 denotes a subject. Reference numeral 802 denotes a moving restricted area of the optical head portion 208. Because the optical head portion 208 is operated inside the moving restricted area 802, a distance between the subject and the optical head is maintained appropriately. The movement of the optical head 208 is performed in a manner that each axis of the XYZ table (not shown) to which the optical head 208 is fixed is moved by a stepping motor and a feed screw (not shown), and a position of an origin of each axis is grasped by an origin detection switch (not shown).

FIG. 8A is a diagram in which the fundus is being photographed. FIG. 8B is a diagram in which the barrel 501 is screwed and attached into the filter thread of the objective barrel for photographing the anterior segment. In this case, the moving amount of the optical head 208 is changed by the volume of the barrel 501 so that the barrel 501 is moved inside the moving restricted area 802.

Figure 9:
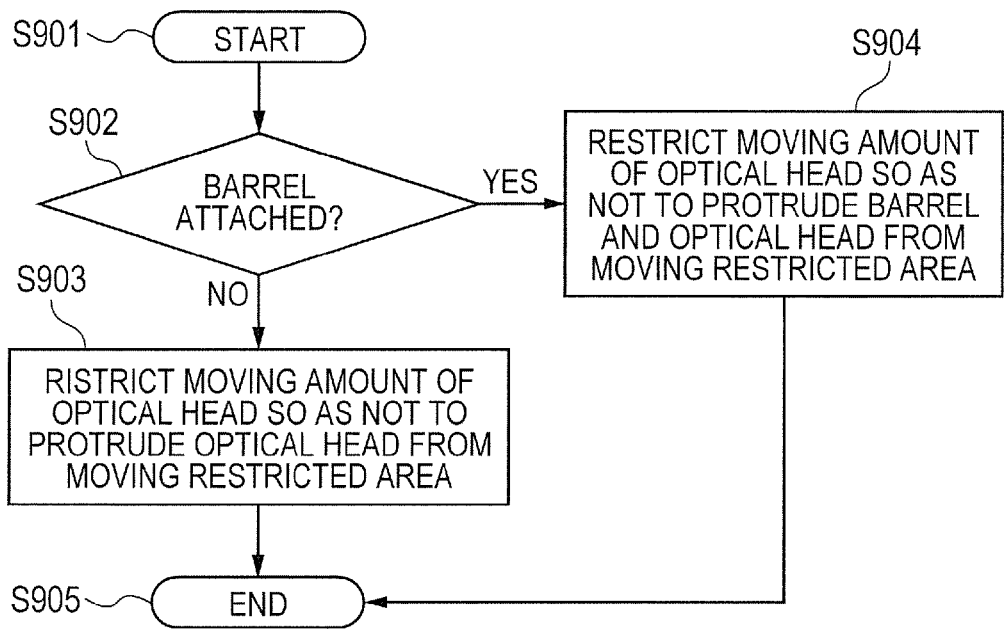
FIG. 9 is a diagram illustrating an operation flow of the ophthalmologic apparatus according to the third embodiment of the present invention.

FIG. 9 is an operation flowchart. In S901, the CPU instructs the start of the flow. In S902, the determining unit determines whether or not the barrel 501 is attached to the objective barrel unit 401 of the optical head 208. In a case where the barrel 501 is attached, the process proceeds to S904. In a case where the barrel 501 is not attached, the process proceeds to S903. In S904, the control unit restricts the moving amount of the optical head 208 so that the barrel 501 and the optical head 208 are not outside the moving restricted area 802. In S903, the control unit restricts the moving amount of the optical head 208 so that the optical head 208 is not outside the moving restricted area 802. S905 is the end of the flow. Finally, a moving unit of the optical head 208 is described as the configuration of the stepping motor, but may be any unit as long as the moving unit of the optical head 208 can be restricted in a case where the attachment of the barrel 501 is detected.

As described above, even when an anterior segment attachment member is attached, a movement area of the optical head can be changed to be different from the movement area in a case where a fundus photographing mode or the like other than the anterior segment photographing mode is selected. In addition, it is preferred to set the movement area of the optical head portion 208 in a case where the anterior segment photographing mode is selected to be smaller than the movement area in a case where a fundus photographing mode or the like other than the anterior segment photographing mode is selected. Thus, a distance between the subject and the apparatus can be maintained appropriately. Therefore, ease of operation by the inspector is improved (the inspector can easily operate the apparatus). Note that, these settings of the moving restricted area of the optical head are performed by a module region functioning as an area changing unit for changing the moving restricted area of the optical head in the CPU or the personal computer 209 performing the above-mentioned flow. In addition, in this embodiment, in a case where the determining unit determines at least any one of the state in which the anterior segment photographing mode is selected and the state in which the attachment member is attached to the ophthalmologic apparatus, the predetermined operation performed by the control unit is to change the moving restricted area of the optical head.

Fourth Embodiment

Figure 10:
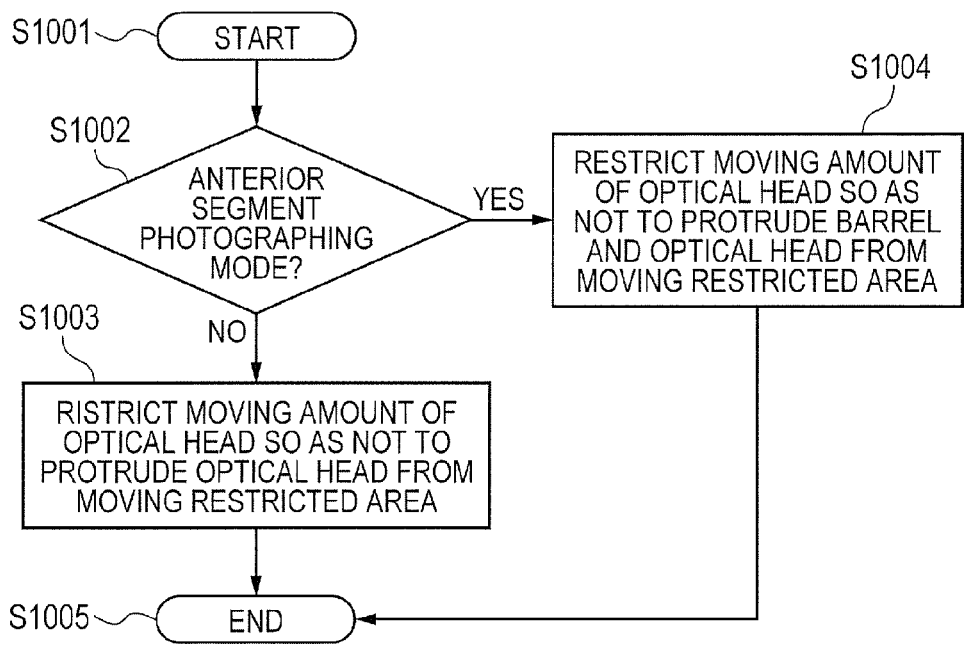
FIG. 10 is a diagram illustrating an operation flow of an ophthalmologic apparatus according to a fourth embodiment of the present invention.

With reference to the drawings, a fourth embodiment of the present invention is described. The ophthalmologic apparatus according to this embodiment has the same configuration as that described in the third embodiment and is different in the operation flow as illustrated in FIG. 10.

In this flow, the CPU (control unit) starts the flow in S1001. In S1002, the determining unit determines whether or not the anterior segment photographing mode is selected. In a case where the anterior segment photographing mode is selected, the process proceeds to S1004. In a case where the anterior segment photographing mode is not selected, the process proceeds to S1003. In S1004, the control unit restricts the moving amount of the optical head 208 so that the barrel 501 and the optical head 208 are not outside the moving restricted area 802.

In S1003, the control unit restricts the moving amount of the optical head 208 so that the optical head 208 is not outside the moving restricted area 802. S1005 is the end of the flow.

Fifth Embodiment

With reference to the drawings, a fifth embodiment of the present invention is described. A configuration of an ophthalmologic apparatus according to the fifth embodiment is different from the ophthalmologic apparatus according to the third embodiment in that a lens (not shown) corresponding to the barrel 501 is insertable and removable from the optical path 333 of the OCT optical system of FIG. 3 by an insertion/removal mechanism (not shown), and in a flow part of the insertion and removal of the lens. Further, the configuration is also different in that when the lens (not shown) corresponding to the barrel 501 is inserted in the optical path 333 of the OCT optical system of FIG. 3, a working distance to the subject (a distance between the corneal apex of the eye to be inspected and the objective lens) becomes longer than that in the fundus photography by 10 mm (hereinafter the distance is referred to as a difference distance). As to the insertion/removal flow of the lens (not shown) corresponding to the barrel 501 to the optical path 333 of the OCT optical system, in a case where the inspection set 115 is switched to the anterior segment photographing mode, the lens (not shown) is inserted in the optical path 333 of the OCT optical system. In a case where the inspection set 115 is set to a mode other than the anterior segment photographing mode, the lens (not shown) is removed from the optical path 333 of the OCT optical system. The flowchart thereof is omitted.

Figure 11A:
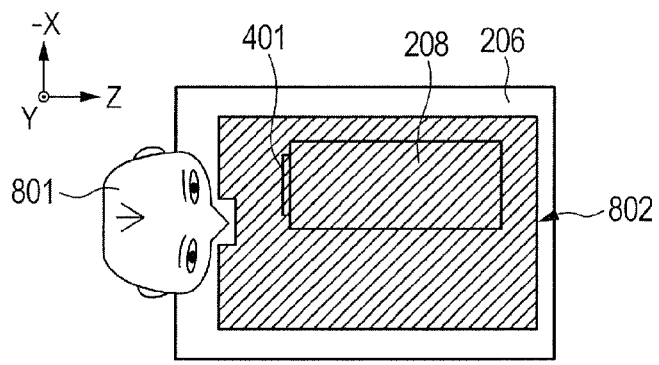
FIGS. 11A and 11B are top views illustrating a schematic configuration of a main body of an ophthalmologic apparatus according to a fifth embodiment of the present invention.
Figure 11B:
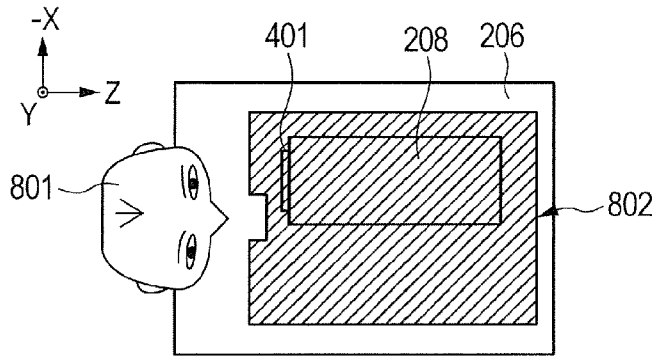

In a case where the inspection set 115 is set to the anterior segment photographing mode in the above-mentioned configuration, the movement area of the optical head portion 208 is changed by the difference distance (the movement area of the optical head portion 208 is changed to be different from the movement area in a case where a fundus photographing mode or the like other than the anterior segment photographing mode is selected). FIG. 11A illustrates a movement area 802 of the optical head portion 208 in a mode other than the anterior segment photographing mode, and FIG. 11B illustrates a movement area 802 of the optical head portion 208 in the anterior segment photographing mode. In the above-mentioned example, there is described an example of changing the movement area of the optical head portion 208 by the mechanism for inserting and removing the optical element in the optical path inside the apparatus main body. Here, in a case where the anterior segment photographing mode is selected, the movement area of the optical head portion 208 is changed to be smaller than the movement area in a case where the fundus photographing mode or the like other than the anterior segment photographing mode is selected. As described above, also in the case where the anterior segment attachment member is attached, ease of operation by the inspector is improved (the inspector can easily operate the apparatus) by changing the moving restricted area of the optical head so that the distance between the subject and the apparatus is maintained appropriately.

Sixth Embodiment

Figure 12:
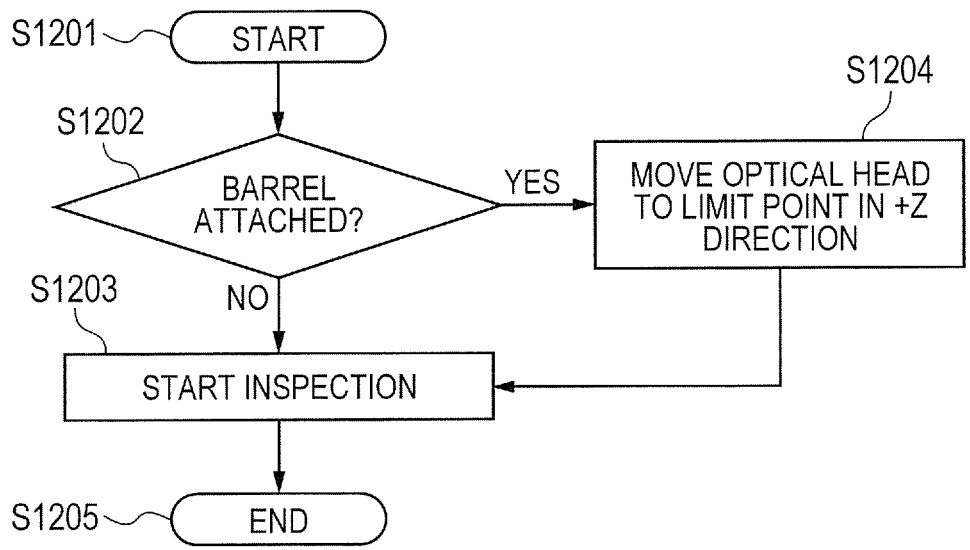
FIG. 12 is a diagram illustrating an operation flow of an ophthalmologic apparatus according to a sixth embodiment of the present invention.

With reference to the drawings, a sixth embodiment of the present invention is described. An ophthalmologic apparatus according to the sixth embodiment has the same configuration as the ophthalmologic apparatus according to the third embodiment but has a different flow illustrated in FIG. 12, which is described below. In S1201, the control unit instructs the start of the flow. In S1202, the determining unit determines whether or not the barrel 501 is attached. In a case where the barrel 501 is attached, the process proceeds to S1204. In a case where the barrel 501 is not attached, the process proceeds to S1203. In S1204, the control unit moves the optical head 208 to a limit point in a +Z direction. Then, the process proceeds to S1203. In S1203, an instruction to start the inspection is issued by the control unit.

As described above, in a case where it is detected that the attachment member related to the anterior segment photography is attached, the optical head is moved away from the subject so that an oppressive feeling of the subject can be reduced. Further, because an operational error by the inspector can be suppressed, ease of operation by the inspector is improved (the inspector can easily operate the apparatus). In other words, in this embodiment, as the attachment member, the anterior segment attachment lens (anterior segment photographing lens 332) is exemplified. In addition, in a case where the determining unit determines that the anterior segment photographing mode is selected and that the anterior segment attachment lens is attached to the ophthalmologic apparatus, the control unit moves the optical head to a position most apart from the subject by the optical head moving unit as the predetermined operation. Note that, the optical head described here corresponds to a configuration in which irradiation of the anterior segment with light and reception of the reflected light from the anterior segment are performed in the above-mentioned ophthalmologic apparatus. The optical head moving unit corresponds to a configuration for moving the above-mentioned optical head particularly in the Z direction.

Seventh Embodiment

Figure 13:
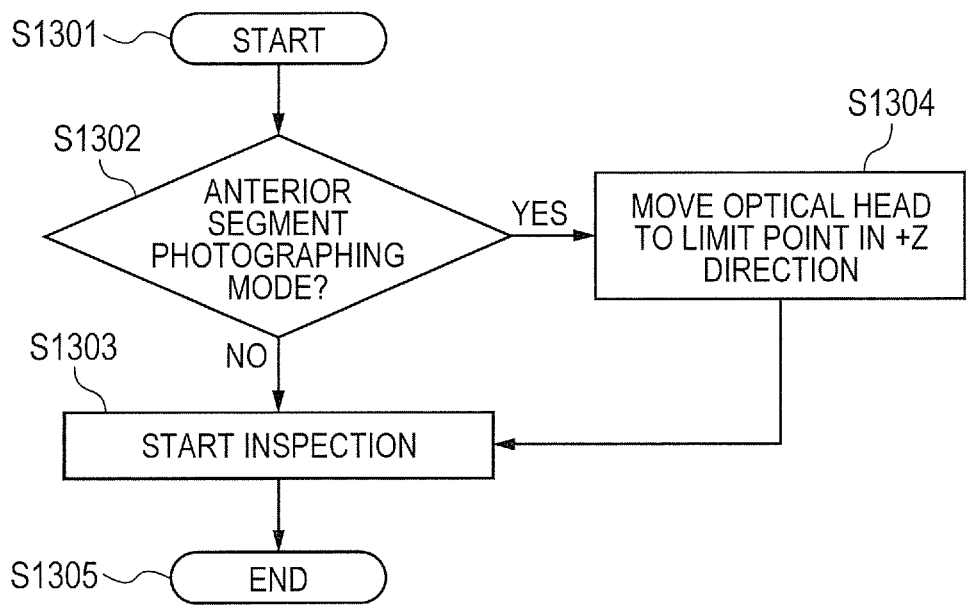
FIG. 13 is a diagram illustrating an operation flow of an ophthalmologic apparatus according to a seventh embodiment of the present invention.

With reference to the drawings, a seventh embodiment of the present invention is described. An ophthalmologic apparatus according to the seventh embodiment has the same configuration as the ophthalmologic apparatus according to the third embodiment but has a different flow illustrated in FIG. 13, which is described below. In S1301, the program starts. In S1302, it is determined whether or not the inspection set 115 is set to the anterior segment photographing mode. In a case where the barrel 501 is attached, the process proceeds to S1304. In a case where the barrel 501 is not attached, the process proceeds to S1303. In S1304, the optical head 208 is moved to the limit point in the +Z direction. Then, the process proceeds to S1303. In S1303, the inspection is started.

As described above, when it is detected that the attachment member related to the anterior segment photography is attached, the optical head is moved away from the subject so that an oppressive feeling of the subject can be reduced. Further, because an operational error by the inspector can be suppressed, ease of operation by the inspector is improved (the inspector can easily operate the apparatus).

Other Embodiments

In addition, the present invention can be realized also by performing the following process. Specifically, software (program) for realizing the functions of the above-mentioned embodiments is supplied to a system or an apparatus via a network or various storage media, and a computer (or CPU, MPU, or the like) of the system or the apparatus reads and executes the program.

As described above, in the ophthalmologic apparatus according to one embodiment of the present invention, in a case there the anterior segment photographing mode is selected, it can be certainly recognized that an object to be attached for the anterior segment photography is not attached. In addition, in the ophthalmologic apparatus according to one embodiment of the present invention, in a case where a mode other than the anterior segment photographing mode is selected after the anterior segment photographing mode, it can be certainly recognized that the object to be attached for the anterior segment photography is attached. In addition, in the ophthalmologic apparatus according to one embodiment of the present invention, because the moving restricted area is switched in a case where the anterior segment photographing mode is selected, a distance between the subject and the apparatus is maintained appropriately, and hence ease of operation by the inspector is improved (the inspector can easily operate the apparatus). In addition, in the ophthalmologic apparatus according to one embodiment of the present invention, because an operational error by the inspector can be suppressed by moving the apparatus away from the subject in a case where the anterior segment photographing mode is selected, ease of operation by the inspector is improved (the inspector can easily operate the apparatus).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent configurations and functions.

This application claims the benefit of Japanese Patent Application No. 2012-014648, filed Jan. 26, 2012, which is hereby incorporated by reference herein in its entirety.

What is claimed is:

1. An ophthalmologic apparatus including an optical system configured to acquire an image of an eye to be inspected, the ophthalmologic apparatus comprising:
    a photographing mode selecting unit configured to select one of (a) an anterior segment photographing mode for photographing, by using the optical system, an anterior segment of the eye to be inspected, and (b) a fundus photographing mode for photographing, by using the optical system, a fundus of the eye to be inspected;
    a moving unit configured to move an optical unit including the optical system, with respect to the eye to be inspected; and
    an area changing unit configured to change a movement area of the optical unit in a case where the anterior segment photographing mode is selected to be smaller than a movement area in a case where the fundus photographing mode is selected.

2. An ophthalmologic apparatus according to claim 1, wherein the anterior segment photographing mode is a mode for photographing a tomographic image of the anterior ocular segment by using the optical system, and
    wherein the fundus photographing mode is a mode for photographing a tomographic image of the fundus by using the optical system.

3. An ophthalmologic apparatus according to claim 1, further comprising:
    a first objective lens disposed in the optical path of the optical system; and a determining unit configured to determine whether or not a second objective lens which is an objective lens for an anterior segment exists in the optical path on a side closer to the eye to be inspected than the first objective lens, wherein, in a case where it is determined that the anterior segment photographing mode is selected and that the second objective lens exists, the area changing unit changes the movement area of the optical unit.

4. An ophthalmologic apparatus according to claim 3, wherein the determining unit determines whether a barrel unit having the second objective lens is attached in or detached from the optical path on the side closer to the eye to be inspected than the first objective lens.

5. An ophthalmologic apparatus according to claim 3, wherein the second objective lens for an anterior segment can be inserted and removed, and wherein the determining unit determines whether the second objective lens is inserted in or removed from the optical path on the side closer to the eye to be inspected than the first objective lens.

6. An ophthalmologic apparatus according to claim 1, further comprising a control unit configured to control the moving unit so that the optical unit moves in a direction away from the eye to be inspected in a case where the anterior segment photographing mode is selected.

7. A method of controlling an ophthalmologic apparatus including an optical system for acquiring an image of an eye to be inspected, the method comprising the steps of:

selecting one of (a) an anterior segment photographing mode for photographing, by using the optical system, an anterior segment of the eye to be inspected, and (b) a fundus photographing mode for photographing, by using the optical system, a fundus of the eye to be inspected;

changing a movement area of an optical unit including the optical system in a case where the anterior segment photographing mode for photographing an anterior segment of the eye to be inspected is selected to be smaller than a movement area in a case where the fundus photographing mode is selected.

8. A method of controlling an ophthalmologic apparatus according to claim 7, wherein the anterior segment photographing mode is a mode for photographing a tomographic image of the anterior ocular segment by using the optical system, and wherein the fundus photographing mode is a mode for photographing a tomographic image of the fundus by using the optical system.

9. A method of controlling an ophthalmologic apparatus according to claim 7, further comprising a step of determining whether or not a second objective lens which is an objective lens for an anterior segment exists in an optical path on a side closer to the eye to be inspected than a first objective lens disposed in an optical path of the optical system, wherein the step of changing includes changing the movement area of the optical unit in a case where it is determined that (a) the anterior segment photographing mode is selected and (b) the second objective lens exists.

10. A non-transitory tangible medium storing a program for causing a computer to perform each step of the method of controlling an ophthalmologic apparatus according to claim 7.

11. An ophthalmologic apparatus according to claim 1, further comprising:

a first objective lens disposed in the optical path of the optical system;

a determining unit configured to determine whether or not a second objective lens which is an objective lens for an anterior segment exists in the optical path on a side closer to the eye to be inspected than the first objective lens; and an acquiring instruction control unit configured to determine whether an acquiring instruction for instructing an image acquisition is enabled or not based on a determination result of the determining unit, in a case where the anterior segment photographing mode is selected by the photographing mode selecting unit.

12. An ophthalmologic apparatus according to claim 11, wherein the acquiring instruction control unit does not enable the acquiring instruction for instructing the image acquisition, in a case where the determining unit determines that the second objective lens does not exist in the optical path on a side closer to the eye to be inspected than the first objective lens.

* * * * *